United States Patent
Gallaher et al.

(10) Patent No.: US 10,232,048 B1
(45) Date of Patent: Mar. 19, 2019

(54) APITHERAPY METHOD AND COMPOSITION

(71) Applicant: Divine Api-Logics, LLC, Farmington, MO (US)

(72) Inventors: Harold Dean Gallaher, Farmington, MO (US); Amanda Jolene Hutchings, Sainte Genevieve, MO (US)

(73) Assignee: Divine Api-Logics, LLC, Farmington, MO (US)

( * ) Notice: Subject to any disclaimer, the term of this patent is extended or adjusted under 35 U.S.C. 154(b) by 28 days.

(21) Appl. No.: 14/945,123

(22) Filed: Nov. 18, 2015

Related U.S. Application Data

(60) Provisional application No. 62/081,048, filed on Nov. 18, 2014.

(51) Int. Cl.
| | |
|---|---|
| *A61K 35/583* | (2015.01) |
| *A61K 36/00* | (2006.01) |
| *A61K 47/46* | (2006.01) |
| *A61K 35/64* | (2015.01) |
| *A61K 47/36* | (2006.01) |

(52) U.S. Cl.
CPC ............ *A61K 47/46* (2013.01); *A61K 35/64* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 2,075,390 A | 3/1937 | August | |
| 2,112,828 A | 4/1938 | Bühler | |
| 2,154,934 A | 4/1939 | Hahn | |
| 3,856,936 A | 12/1974 | Vick et al. | |
| 3,898,325 A | 8/1975 | Revici | |
| 4,437,895 A * | 3/1984 | Koulbanis | A61K 8/922 106/245 |
| 4,822,608 A * | 4/1989 | Benton | A61K 38/12 424/114 |
| 4,990,331 A | 2/1991 | Slessor et al. | |
| 5,827,829 A | 10/1998 | Hansen et al. | |
| 5,849,729 A | 12/1998 | Zoumas et al. | |
| 5,886,003 A | 2/1999 | Cohen et al. | |
| 5,958,887 A * | 9/1999 | Hansen | A61K 35/63 424/230.1 |
| 6,074,673 A | 6/2000 | Guillen | |
| 6,106,844 A | 8/2000 | King | |
| 6,395,306 B1 | 5/2002 | Cui et al. | |
| 6,419,940 B1 | 7/2002 | Blanton | |
| 6,482,442 B1 | 11/2002 | Dado | |
| 6,773,700 B2 | 8/2004 | Thoenes | |
| 6,780,416 B1 | 8/2004 | Spertini | |
| 6,894,060 B2 | 5/2005 | Slade | |
| 7,256,254 B2 | 8/2007 | Zimmerman | |
| 7,276,236 B2 | 10/2007 | Pollack | |
| 7,528,112 B2 | 5/2009 | Cunningham et al. | |
| 7,767,234 B2 | 8/2010 | Probasco | |
| 8,021,702 B2 | 9/2011 | Brady | |
| 8,075,897 B2 | 12/2011 | Spertini et al. | |
| 8,440,234 B2 | 5/2013 | Kim | |
| 8,568,790 B2 | 10/2013 | Moloney | |
| 8,637,037 B2 | 1/2014 | Mistrello et al. | |
| 9,415,082 B1 * | 8/2016 | Davis | A61K 36/87 |
| 2003/0118597 A1 | 6/2003 | Abbadi | |
| 2003/0166548 A1 | 9/2003 | Peterson et al. | |
| 2004/0081702 A1 | 4/2004 | Kim | |
| 2004/0253249 A1 | 12/2004 | Rudnic et al. | |
| 2004/0258765 A1 | 12/2004 | Gee | |
| 2007/0110739 A1 | 5/2007 | Logsdon | |
| 2008/0031850 A1 * | 2/2008 | Bader | A61K 35/407 424/85.2 |
| 2008/0096963 A1 | 4/2008 | Jean et al. | |
| 2008/0292715 A1 | 11/2008 | Snow et al. | |
| 2010/0104547 A1 | 4/2010 | Logsdon | |
| 2010/0166878 A1 | 7/2010 | Park et al. | |
| 2011/0059184 A1 | 3/2011 | Hartmann et al. | |
| 2012/0034320 A1 * | 2/2012 | Murray | A61K 31/375 424/678 |
| 2012/0082656 A1 | 4/2012 | Yoon et al. | |
| 2012/0114568 A1 | 5/2012 | Wrenn | |
| 2012/0128784 A1 | 5/2012 | Han et al. | |
| 2012/0213869 A1 * | 8/2012 | Ma | A61K 31/165 424/727 |
| 2014/0037751 A1 | 2/2014 | Kane et al. | |
| 2014/0288166 A1 | 9/2014 | Huang et al. | |
| 2014/0302156 A1 | 10/2014 | Beerman | |
| 2015/0306025 A1 * | 10/2015 | Chen | A61Q 1/04 424/94.1 |

FOREIGN PATENT DOCUMENTS

WO     WO2000053228 A2 *  9/2000

OTHER PUBLICATIONS

Garti et al. (2004) JAOCS, vol. 81, No. 9, 873-877. (Year: 2004).*
Lockey et al. (1990) J. Allergy Clin. Immunol. 86: 775-780. (Year: 1990).*
Park et al. (2015) PLoS ONE: 10(5): e0126971. 26 pages. (Year: 2015).*
Son et al. (2007) Pharmacology and Therapeutics 115: 246-270. (Year: 2007).*
Internet posting from andy.nachbaur@beenet.com regarding Bee Venom Therapy—FAQ, Feb. 4, 1996, 1 page.

* cited by examiner

*Primary Examiner* — Christopher R Tate
*Assistant Examiner* — Russell G Fiebig
(74) *Attorney, Agent, or Firm* — Stinson Leonard Street LLP

(57) ABSTRACT

A bee venom composition and method for preparing such a composition. The bee venom can be placed in a base that allows it to be applied directly to the skin. Skin penetration enhancers promote percutaneous absorption to increase the speed at which the effects of the bee venom are experienced. A skin penetration enhancer is also disclosed.

4 Claims, No Drawings

APITHERAPY METHOD AND COMPOSITION

RELATED APPLICATIONS

This application is the nonprovisional of Provisional Application Ser. No. 62/081,048, filed Nov. 18, 2014, the entire contents of which are incorporated herein by reference.

BACKGROUND

The present invention relates to apitherapy and, more particularly, to an apitherapy method and composition.

Currently, apitherapy is painful and inconvenient. A person must be stung on a regular basis by live bees. Travel is difficult or impossible because of the need for live bees. Bees are temperature sensitive. Opening a hive to collect bees for stinging purposes may harm or even kill the entire colony when the weather is quite cold. For this reason, apitherapy in colder climates is difficult or sometimes impossible.

The quality and quantity of venom injected by a bee during a sting varies with the age of the bee and the seasonal food availability. It is impossible to control how much venom is injected with each live bee sting. It is also impossible to control the quality of venom administered. Whatever amount and strength of venom the bee contains is what will be injected with the sting.

Apitherapy is best carried out when specific locations of the body are stung. This is difficult to control when using live bees.

Previous art includes applying bee venom with the use of a needle injection through the skin. The needle can be painful, may require professional assistance to administer, and may introduce the possibility of infections due to piercing of the skin by the needle. Live bees may also carry infectious materials that can cause infections when the bee's stinger pierces the skin.

Previous art also includes the use of topical ointments. Topical ointments are more typically used for surface cosmetic purposes of the venom and are not intended to carry materials through the skin. The topical ointment is also easily washed or wiped away as it lingers on the surface of the skin rather than being absorbed.

As can be seen, there is a need for an apitherapy method and composition that allows for apitherapy without pain, with reduced danger of infections, without dependence on favorable weather, without the resultant sting or needle marks, using a measured amount and quality of venom, and applied on the correct place on the body.

SUMMARY

In one aspect of the present invention, a bee venom composition comprises a mixture of bee venom, one or more essential plant oils, and an emulsifier.

In another aspect of the present invention, a method of preparing a bee venom composition comprises preparing one or more essential plant oils, suspending dried bee venom in the one or more essential plant oils to form a first intermediate. An emulsifier is added to the first intermediate to create a second intermediate.

In still another aspect of the present invention, a skin penetration enhancer composition comprises Niaouli oil, jojoba oil and a matrix material.

Other objects and features will be in part apparent and in part pointed out hereinafter.

DETAILED DESCRIPTION

Topical substances of the present composition allow percutaneous absorption of bee venom at specific locations on the body where the bee venom can have the most efficacy. Some considerations in providing an efficacious composition may include limiting or eliminating any deleterious effects on the bee venom in the composition process, providing economically efficient compositions, maximizing efficacy of the bee venom, easy use of the composition by a user, natural composition, longer shelf life and correct dosing, to name a few. It will be understood that not all of these considerations need be satisfied by compositions of the present invention.

In one embodiment, a bee venom composition may include essential plant oils that facilitate percutaneous absorption, bee venom, an emulsifier and a base. Although essential plant oils are preferred, other essential oils could be used. The bee venom may be suspended in the essential plant oil and the emulsifier may be added. Preferably, all processing can be carried out with the components already in and/or being added to the composition at about room temperature. In one example, processing was carried out at about 68° F. However, processing may be carried out at temperatures above freezing for the specific components up to about 75° F., more preferably from about 60° F. to about 75° F., and still more preferably between about 68° F. and 75° F. More specifically, essential plant oils including terpene skin penetration enhancers are used. In one embodiment, about 0.5% to about 12% (by volume) of each of Niaouli oil and jojoba oil receive dried honey bee venom ranging from about 0.0005% to 0.05% (by volume) to suspend the bee venom. This creates a first intermediate composition. An emulsifier in the form of soy lechtin is slowly mixed into the essential plant oils suspending the bee venom to create a second intermediate composition. The soy lechtin may be in the quantity of about 3% to 10% (by volume). Excipients may be added for additional stabilization of the first or second intermediate composition. It will be understood that the stated percentage volumes are of the final composition including the essential plant oils, the bee venom, the emulsifier and a matrix material. A suitable matrix material could be corn starch, which also functions as an emulsifier and excipient.

Preferably, one or more of the essential plant oils includes as a component a terpene, which is believed to function as a skin penetration enhancer. For example, Niaouli oil extracted through steam distillation from the leaves and twigs of *Melaleuca quinquenevia*. The main components Niaouli oil are alpha phellandrene, alpha pinene, beta pinene, cineole, gamma terineol, limonene, linalool and piperitone. Beta pinene and limonene are known terpenes. Jojoba oil is a liquid wax ester extracted from the seed of a jojoba plant. Jojoba oil includes Vitamin E and phospholipids. Jojoba oil does not oxidize easily and includes no triglycerides so that it has a long shelf life.

The composition may then be levigated into a base cream. In one example, the base cream is shea butter. The final composition can be applied directed to the skin and rubbed in for delivering bee venom to below the epidermal layers of the body.

The mixture will then be placed in a storage container or applicator. An applicator can be configured to provide a precise predetermined quantity for treating a particular condition. For example, the storage container or applicator may embody a measuring metering system. In certain embodiments, additional scents may be added to the composition to provide a specific scent. When applying the mixture onto a portion of skin, at least one applicator may measure out a dosage amount onto the skin. The user may then rub the mixture into the skin. The composition and method of applying the composition may slow for nausea and lethargy related to various complications to be reduced. The mixture may be pre mixed, or separated for the user to mix prior to application. The mixture, once rubbed into the skin, may enter the bloodstream of the user. Having a precisely measured amount of venom in the mixture may allow for controlled review of the benefits of the absorption of the mixture by the user.

The bee venom combined with a percutaneous permeation enhancer will carry the venom to the bloodstream without the use of live bees, injection needle, or topical lotion. The venom will then be delivered to the bloodstream without pain, injection marks or sting marks. The measuring applicator will help with controlling the dosage used per application.

It has been found that a combination of Niaouli oil and jojoba oil increases the speed at which bee venom is absorbed through the skin. Bee venom has a relatively large molecular weight. Preliminary investigation showed that this combination was 50% faster in producing reported effects than other penetration enhancers and combinations of penetration enhancers. Thus, it this composition is believed to have utility for percutaneous transport of other medicines. In other examples, the concentration of each of Niaouli oil and jojoba oil may be between about 4% and 10% (by volume). Testing indicates an excess of jojoba oil by volume to that of Niaouli oil within the ranges produces good results in skin penetration. In the example described above, the concentration of each of Niaouli oil and jojoba oil was 5.3% and 8% (by volume) respectively.

Apitherapy carried out by this method may also be used with venom from life forms other than bees.

Preliminary testing of about 200 subjects has shown efficacy of the bee venom composition described above in reducing hot flashes, psoriasis, headaches, nausea associated with certain chemotherapy treatments, arthritis, gout, conditions involving inflammation of tissue, joint and neck pain, pain associated with plantar fasciitis, symptoms of multiple sclerosis. In addition, good results have been reported in the treatment of insect bites and poison ivy. The condition for which relief was sought in the subject was arthritis for the majority of subjects. The subjects were asked to apply a pea sized amount of cream (prepared as described above, which is roughly equivalent to one bee sting). Subjects suffering from nausea applied the pea sized amount of cream to the ankle. Reaction time, length of time for which relief was experienced and side effects (if any) were documented. A comparison to the medicine currently being used by the subject from the viewpoint of the subject was also recorded. In certain embodiments, acupuncture sites may be used for the application locations of the mixture. For example relief from hot flashes associated with the onset of menopause has been reported from applying the composition to the bottom of the feet. Relief from nausea, for example associated with cancer treatment, such as chemotherapy, has been reported as effective with application of the composition to the ankles. Separately, fever blisters and rosacea have shown improvement using the cream prepared as described herein.

The bee venom may be extracted, for example, from the bee by use of a mild electrical shock in which the bee may be induced to sting a glass plate placed at the entrance to a hive. The venom may be scraped from the glass plate after the venom dries to a powder. In this way it is possible to collect the venom while minimizing or eliminating harm to the bees.

Having described the invention in detail, it will be apparent that modifications and variations are possible without departing from the scope of the invention defined in the appended claims.

When introducing elements of the present invention or the preferred embodiments(s) thereof, the articles “a”, “an”, “the” and “said” are intended to mean that there are one or more of the elements. The terms “comprising”, “including” and “having” are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description and shown in the accompanying drawings shall be interpreted as illustrative and not in a limiting sense.

What is claimed is:

1. A method of preparing a topical composition for relieving subcutaneous pain, comprising the steps of:

(a) suspending an effective amount of dried bee venom in an effective amount of a skin penetration enhancer composition to form a first intermediate;

(b) adding an emulsifier to the first intermediate to form a second intermediate; and (c) combining the second intermediate with a base cream to form the topical composition, wherein the skin penetration enhancer comprises essential oils of niaouli oil and jojoba oil, and wherein the concentration of niaouli oil is about 5.3% by volume and the concentration of jojoba oil is about 8% by volume of the topical composition.

2. The method as set forth in claim 1 further comprising adding an excipient to the first intermediate.

3. The method as set forth in claim 1 wherein all process steps are carried out at a temperature less than or equal to about 75° F.

4. The method as set forth in claim 3 wherein all process steps are carried out at a temperature in a range of about 68° F. and 75° F.

* * * * *

UNITED STATES PATENT AND TRADEMARK OFFICE
CERTIFICATE OF CORRECTION

| | | |
|---|---|---|
| PATENT NO. | : 10,232,048 B1 | Page 1 of 1 |
| APPLICATION NO. | : 14/945123 | |
| DATED | : March 19, 2019 | |
| INVENTOR(S) | : Gallaher et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 213 days.

Signed and Sealed this
Seventeenth Day of March, 2020

Andrei Iancu
*Director of the United States Patent and Trademark Office*